US008455437B2

(12) United States Patent
Sitkovsky et al.

(10) Patent No.: US 8,455,437 B2
(45) Date of Patent: Jun. 4, 2013

(54) METHOD TO PREDICT AND PREVENT OXYGEN-INDUCED INFLAMMATORY TISSUE INJURY

(75) Inventors: Michail V. Sitkovsky, Boston, MA (US); Manfred Thiel, Eichenau (DE)

(73) Assignee: The United States of America, as Represented by the Secretary of the Department of Health and Human Services, Washington, DC (US)

( * ) Notice: Subject to any disclaimer, the term of this patent is extended or adjusted under 35 U.S.C. 154(b) by 1377 days.

(21) Appl. No.: 11/339,208

(22) Filed: Jan. 25, 2006

(65) Prior Publication Data

US 2007/0053993 A1 Mar. 8, 2007

Related U.S. Application Data

(60) Provisional application No. 60/650,267, filed on Feb. 4, 2005.

(51) Int. Cl.
*A61P 29/00* (2006.01)
*A61K 33/00* (2006.01)

(52) U.S. Cl.
USPC ......................................... 514/12.2; 424/600

(58) Field of Classification Search
None
See application file for complete search history.

(56) References Cited

U.S. PATENT DOCUMENTS

| | | | |
|---|---|---|---|
| 5,635,530 A | 6/1997 | Mechoulam et al. | |
| 6,051,566 A | 4/2000 | Bianco | |
| 6,589,948 B1 * | 7/2003 | Malfroy-Camine et al. . | 514/185 |
| 6,844,317 B2 * | 1/2005 | Winslow et al. ............. | 514/13.4 |
| 6,919,082 B2 * | 7/2005 | Shirasu et al. ........... | 424/195.16 |
| 2009/0029967 A1 * | 1/2009 | Grzelak et al. ........... | 514/211.13 |

FOREIGN PATENT DOCUMENTS

| | | |
|---|---|---|
| JP | 200523064 | 1/2005 |
| WO | 03/047628 A1 | 6/2003 |

OTHER PUBLICATIONS

Werns et al. Cardiovascular Drugs and Therapy 2: 761-769, 1989.*
Kanwar et al. Am J Physiol Gastrointest Liver Physiol 275:212-218, 1998.*
Sukoff Mh.. J Neurosurg. 2001 Sep. 95(3):544-6.*
Shikunova L. G. Bulletin of Experimental Biology and Medicine vol. 44, No. 3 / Sep. 1957 1054-1057.*
Warrell et al. Oxford Textbook of Medicine 4th Ed. vol. 2 Oxford; New York: Oxford University Press, 2003.*
(http://cancerweb.ncl.ac.uk/omd/) The online medical dictionary.*
George et al., Effects of lisofylline on hyperoxia-induced lung injury, Am. J. Physiol. Lung Cell Mol. Physiol., 276: L776-L785, 1999.*
Yasui et al., Theophylline induces neutrophil apaptosi through adenosine A2A receptor antagonism, Journal of Leukocyte Biology, 67: 529-535, 2000.*
Plafki (Aviation, Space and Environmental Medicine 2000, 71, 119-124).*
Bateman (British Medical Journal 1998, 317, 798-801).*
Boyle et al., (New Zealand Medical Journal Jul. 2006, 119).*
Jackson et al., (Angiogenesis and Inflammation, 11, 457-465, 1997).*
Definition of prevent from Oxford English dictionary online version accessed on Aug. 27, 2012.*
Morello et al. (Journal of Receptor , Ligand and Channel Research 2, 11-17, 2009) Adenosine A2a receptor . . . .*
Uhlig, S., et al., Pharmacological interventions in ventilator-induced lung injury, TRENDS in Pharmacological Sciences, 25(11): 592-600 (2004).
Davis, J. M., et al., Prophylactic effects of dexamethasone in lung injury caused by hyperoxia and hyperventilation, American Physiological Society, 72(4): 1320-1325 (1992).
Ohta, N., et al., Glucocorticoid suppresses neutrophil activation in ventilator-induced lung injury, Crit. Care Med., 29 (5): 1012-1016 (2001).
Ross, S. D., et al., Selective Adenosine-A2A Activation Reduces Lung Reperfusion Injury Following Transplantation, J. Heart & Lung Transplantation, 18(1): 72 (1999) (Abstract).
Rubini, F., et al., Acute Effect of Corticosteroids on Respiratory Mechanics in Mechanically Ventilated Patients with Chronic Airflow Obstruction and Acute Respiratory Failure, Am. J. Respir. Crit. Care Med., 149: 306-310 (1994).
Datacase WPI Week 199841, Thomson Scientific, London, GB, AN 1998-479518, XP002579773 & RU 2 105 555 (1998).
Nava, S., et al., Controlled Short-term Trial of Fluticasone Propionate in Ventilator-Dependent Patients with COPD, Chest, 118(4): 990-999 (2000).
Sullivan, G. W., Adenosine A2a receptor agonists as antil-inflammatory agents, Current Opinion in Investigational Drugs, 4(11): 1313-1319 (2003).
Sitkovsky, M. V., et al., Physiological Control of Immune Response and Inflammatory Tissue Damage by Hypoxia-Inducible Factors and Adenosine A2a Receptors, Annu. Rev. Immunol., 22: 657-682 (2004).
Webb, R. L., et al., CGS 21680-A Potent Selective Adenosine A2 Receptor Agonist, Cardiovascular Drug Reviews, 10 (1): 26-53 (1992).
Thiel, M., et al., "Oxygenation Inhibits the Physiological Tissue-Protecting Mechanism and Thereby Exacerbates Acute Inflammatory Lung Injury," PLoS Biology, 3(6): 1088-1100 (2005).
Weilemann, L. S., et al., "The effect of Cortisone on the course of respiratory and clinical parameters in ventilator patients with imminent ARDS," Schweizerische Medizinische Wochenschrift, 116(17): 574-579 (1986).

(Continued)

*Primary Examiner* — David J Blanchard
*Assistant Examiner* — Tigabu Kassa
(74) *Attorney, Agent, or Firm* — Elmore Patent Law Group, P.C.; Darlene A. Vanstone, Esq.; Carolyn S. Elmore, Esq.

(57) ABSTRACT

Methods for modulating responsiveness to increased oxygen levels in an at-risk subject identifying an at-risk subject; and before exposing the identified at-risk subject to an increased amount of oxygen, administering to the at-risk subject an anti-inflammatory agent wherein the responsiveness of the at-risk subject to said increased amount of oxygen is modulated as compared to the responsiveness of the at-risk subject to said increased amount of oxygen in the absence of said anti-inflammatory.

9 Claims, 4 Drawing Sheets

OTHER PUBLICATIONS

Das, et al., "Role of polymorphonuclear leukocytes in hyperoxic lung injury. Prevention of neutrophil influx into the lung endothelium during oxygen exposure by ibuprofen," Biomed Biochim Acta., 47(12): 1023-1036 (1988).

Hey, S. D., et al., "A study of a complex ARDS patient," Dynamics, 14(4): 22-28 (2003).

Sanders, et al., "Two doses of early intravenous dexamethasone for the prevention of bronchopulmonary dysplasia in babies with respiratory distress syndrome," Pediatr. Res., 36(1 Pt 1): 122-128 (1994).

Ohta, A., et al., "Role of G-protein-coupled adenosine receptors in downregulation of inflammation and protection from tissue damage," Nature, 414 (20/27): 916-920 (2001).

Bellingan, G., "Hooray for Hypoxia? A new study comes to a counter-intuitive conclusion: hypoxia may have its benefits for patients with lung injury," PLoS Medicine, 2(6): 0480-0482 (2005).

Thiel, et al., "An Update on Recent Industry Initiatives," International Journal of Respiratory Care, p. 42 (2005).

"Excess Oxygen Worsens Lung Inflammation in Mice" Press Release by the National Institute of Allergy and Infectious Diseases, pp. 1-2 (2005).

Uhlig, et al., "Pharmacological Interventions in Ventilator-Induced Lung Injury," Trends in Pharmacological Sciences, 25(11):592-600, 2004.

Anderson, et al., "Accelerated resequestration of cytosolic calcium and suppression of the pro-inflammatory activities of human neutrophils by CGS21680 in vitro," British Journal of Pharmacology, 130:717-724, 2000.

* cited by examiner

METHOD TO PREDICT AND PREVENT OXYGEN-INDUCED INFLAMMATORY TISSUE INJURY

RELATED APPLICATION

This application claims the benefit of U.S. Provisional Application No. 60/650,267, filed on Feb. 4, 2005. The entire teachings of the above application are incorporated herein by reference.

GOVERNMENT INTEREST

The present invention was made with the assistance of U.S. Government funding. The U.S. Government has certain rights in this invention.

FIELD

This application relates to the fields of oxygen therapy and immune response and use of higher than 21% oxygen-containing gas mixtures during therapeutic and prophylactic procedures. This application also relates to the prevention of oxygen induced exacerbation of inflammation and organ damage due to the interruption by oxygen of physiological anti-inflammatory mechanism.

BACKGROUND

Mammals require molecular oxygen for essential metabolic processes including e.g. oxidative phosphorylation in which oxygen serves as electron acceptor during ATP formation. The lack of oxygen is not tolerated and mammals including humans are critically dependent on the oxygen supply by lungs. Therefore, intubation and mechanical ventilation represent one of the most widely used prophylactic and therapeutic clinical interventions to counteract the insufficient pulmonary oxygen-delivering capacity of patients who suffer from severe lung inflammation or other pathologies.

Many clinical conditions, including aspiration, trauma, and hemorrhagic shock are frequently followed by pulmonary and systemic infectious and septic complications that lead to pulmonary dysfunction and subsequent lung failure. Acute lung injury (ALI) or its more severe form, the Acute Respiratory Distress Syndrome (ARDS) occur with a frequency of approximately 130,000 cases and more than 50,000 deaths from ARDS per year only in the United States.

Although the majority of patients respond well to oxygen therapy with oxygen toxicity being an uncommon occurrence in intensive care medicine, there still remains the possibility that oxygen therapy may be suboptimal in ARDS patients as it may promote deleterious pulmonary inflammation, which fuels this disease process. Since the magnitude and duration of lung inflammation was shown to determine the final outcome of ARDS patients, it is important to avoid the possible adverse effects of oxygen on inflammatory processes. Day Y J, Marshall M A, Huang L, McDuffie M J, Okusa M D and Linden J. *Protection from ischemic liver injury by activation of A2A adenosine receptors during reperfusion: inhibition of chemokine induction, Am J Physiol Gastrointest Liver Physiol*, 286: G285-G293, 2004; Sullivan G W, Lee D D, Ross W G, DiVietro J A, Lappas C M, Lawrence M B and Linden J. *Activation of A2A adenosine receptors inhibits expression of {alpha}4/{beta}1 integrin (very late antigen-4) on stimulated human neutrophils, J Leukoc Biol*, 75: 127-134, 2004; Day Y J, Huang L, McDuffie M J, Rosin D L, Ye H, Chen J F, Schwarzschild M A, Fink J S, Linden J and Okusa M D. *Renal protection from ischemia mediated by A2A adenosine receptors on bone marrow-derived cells, J Clin Invest*, 112: 883-891, 2003; and Platts S H, Linden J and Duling B R. *Rapid modification of the glycocalx caused by ischemia-reperfusion is inhibited by adenosine A2A receptor activation, Am J Physiol Heart Circ Physiol*, 284: H2360-H2367, 2003.

SUMMARY

The invention is a method to eliminate dangers of oxygen therapy by treating a subject in need thereof to decrease one or more indicia of inflammation and either cell mediated immunity or humoral immunity, during and/or before or after the oxygen therapy, comprising the step of administering an effective amount of at least one anti-inflammatory compound to the subject under conditions suitable for inducing said decrease in said indicia, wherein said hypoxia to adenosine activation to A2 adenosine receptor pathway interrupting compound is selected from the group consisting of a compound capable of inhibiting accumulation of adenosine, expression and functions of A2 adenosine receptor, a compound which inhibits A2 receptor and compound which interferes with A2 receptor gene expression, and a compound which inhibits inflammatory processes. Also disclosed, is a method for modulating responsiveness to increased oxygen levels in an at-risk subject comprising screening for an at-risk subject; identifying an at-risk subject; and before exposing the identified at-risk subject to an increased amount of oxygen, administering to the at-risk subject an anti-inflammatory agent wherein the responsiveness of the at-risk subject to said increased amount of oxygen is modulated as compared to the responsiveness of the at-risk subject to said increased amount of oxygen in the absence of said anti-inflammatory. In accordance with the invention, increased amounts of oxygen may be administered to an at-risk subject by, for example, inhalation or by placing the subject in a suitable chamber or room with levels of oxygen being higher than ambient levels, or by placing the subject in a suitable hyperbaric chamber with levels of oxygen being higher than ambient level, a therapy also referred to herein as "hyperbaric oxygen therapy" (HBOT). The invention also provides for administering increased amounts of oxygen to an at-risk subject by injecting the subject intravenously with oxygen-saturated blood or blood products, including synthetic blood components.

Applicants predicted that lung tissues are protected from overactive immune cells by the same hypoxia-driven mechanism and immunosuppressive $A_{2A}$ adenosine receptors $(A_{2A}R)$-mediated mechanism that was recently shown to play a critical role in the downregulation of inflammation and tissue damage in different models. Accordingly, in the pathogenesis of acute lung injury it is suggested that bacterial toxins-activated immune cells (e.g. granulocytes) cause collateral lung tissue damage with impairment of the local microcirculation and blood supply. The ensuing tissue damage-associated hypoxia facilitates the accumulation of extracellular adenosine, which then triggers immunosuppressive $A_{2A}R$ on activated immune cells. This leads to the accumulation of immunosuppressive intracellular cAMP that, in turn, inhibits signaling pathways that are required for synthesis and secretion of pro-inflammatory and cytotoxic mediators by immune cells, thereby protecting remaining healthy tissues from continuing immune damage. Since this described physiological tissue-protecting mechanism depends on the hypoxia produced extracellular adenosine, and since the oxygenation of lungs in intubated patients is performed to increase oxygen tension—thereby abolishing hypoxia and disrupting the adenosine accumulation—, we reasoned that such interruption of the hypoxia→adenosine→$A_{2A}R$ pathway by oxygenation could lead to a disengagement of the critical tissue protecting mechanism and to unintended exaggeration of inflammatory lung damage (iatrogenic disease). Thus, oxygenation may eliminate this lung protecting pathway and together with direct oxygen toxicity may contribute to pulmonary complications.

Applicants predicted that in several in vivo models of lung infection and inflammation, oxygenation does indeed strongly exacerbate the inflammatory lung damage and accelerate mice death by the interruption of the hypoxia→adenosine→$A_{2A}R$ pathway. These deleterious effects of oxygenation are preventable since an exogenously added anti-inflammatory, for example, synthetic $A_{2A}R$ agonist, compensated for the loss of endogenously formed adenosine in inflamed lungs of oxygenated mice and thereby prevented lung injury and rescued mice from death.

In the practice of the method, at least one A2 receptor and/or extracellular adenosine levels-affecting compound is administered to a subject under conditions effective to decrease a number, a percentage, a ratio of percentages or an activity of blood cells in a sample of a biological fluid or a tissue from a pre-treatment value to a lower post-treatment value or effective to decrease a concentration of a blood protein in a sample of biological fluid from a pre-treatment value to a lower post-treatment value. The blood cells can be selected from among leukocytes, lymphocytes, monocytes, T-lymphocytes, B-lymphocytes, stem cells, $CD2^+$-lymphocytes, $CD4^+$-lymphorytes, $CD8^+$-lymphocytes, $CD19^+$-lymphocytes, plasma cells, neutrophils, stab neutrophils, segmented neutrophils, basophils, eosinophils, platelets, and erythrocytes.

The method should be used in a wide variety of clinical situations including not only patients with inflamed lungs and bronchi (for example, ARDS, COPD, and asthma) but also patients with infectious diseases and trauma, for example, trauma associated with an accident or surgery. In one embodiment, the method of the invention minimizes or prevents ischemia-reperfusion induced inflammatory tissue injury. The anti-inflammatory is administered systemically or locally as indicated by the specific inflammatory condition(s) present. For example where tissue injury is likely to be local, such as with ischemic-reperfusion injury, the local administration of an anti-inflammatory agent is preferred prior to the administration of the increased amount of oxygen.

Some suitable methods for screening individuals for inflammatory conditions are known. For example, one screening method of the invention is measuring the blood protein levels. Blood proteins associated with the presence of inflammation in a subject include, but are not limited to, immunoglobulin, a lysozyme, a cytokine, an interferon, a complement protein, a coagulation protein, an fibrinolytic system protein, an enzyme inhibitor, a bradykinin system protein, a hormone, a cytokine, and a receptor protein. Other tests for the presence of inflammation may be employed such as the visible indicia of inflammation (e.g., redness, swelling and pain) or blood counts.

In one embodiment, the method further comprises administering the at least one A2 receptor and/or extracellular adenosine levels-affecting compound to the at-risk subject under conditions effective to decrease a number or a percentage of blood cells, especially while blood cells, in a sample of biological fluid and/or to decrease the pro-inflammatory effector functions of immune and non-immune cells. Normal levels of white blood cells, especially lymphocytes, monocytes and granulocytes, are known.

In another embodiment, the invention is a method to protection from the pathogen-induced tissue by administering an A2 receptor and/or extracellular adenosine levels-affecting compound. Suitable anti-inflammatory agents include adenosine kinase inhibitors, a bioactive agent which de-stabilizes expression of A2 receptor and a bioactive agent which prevents A2 receptor expression and functions. In one embodiment, said A2 receptor and/or extracellular adenosine levels-affecting compound is a small interfering RNA (siRNA) or a ribozyme.

DETAILED DESCRIPTION OF THE INVENTION

Figure 1:
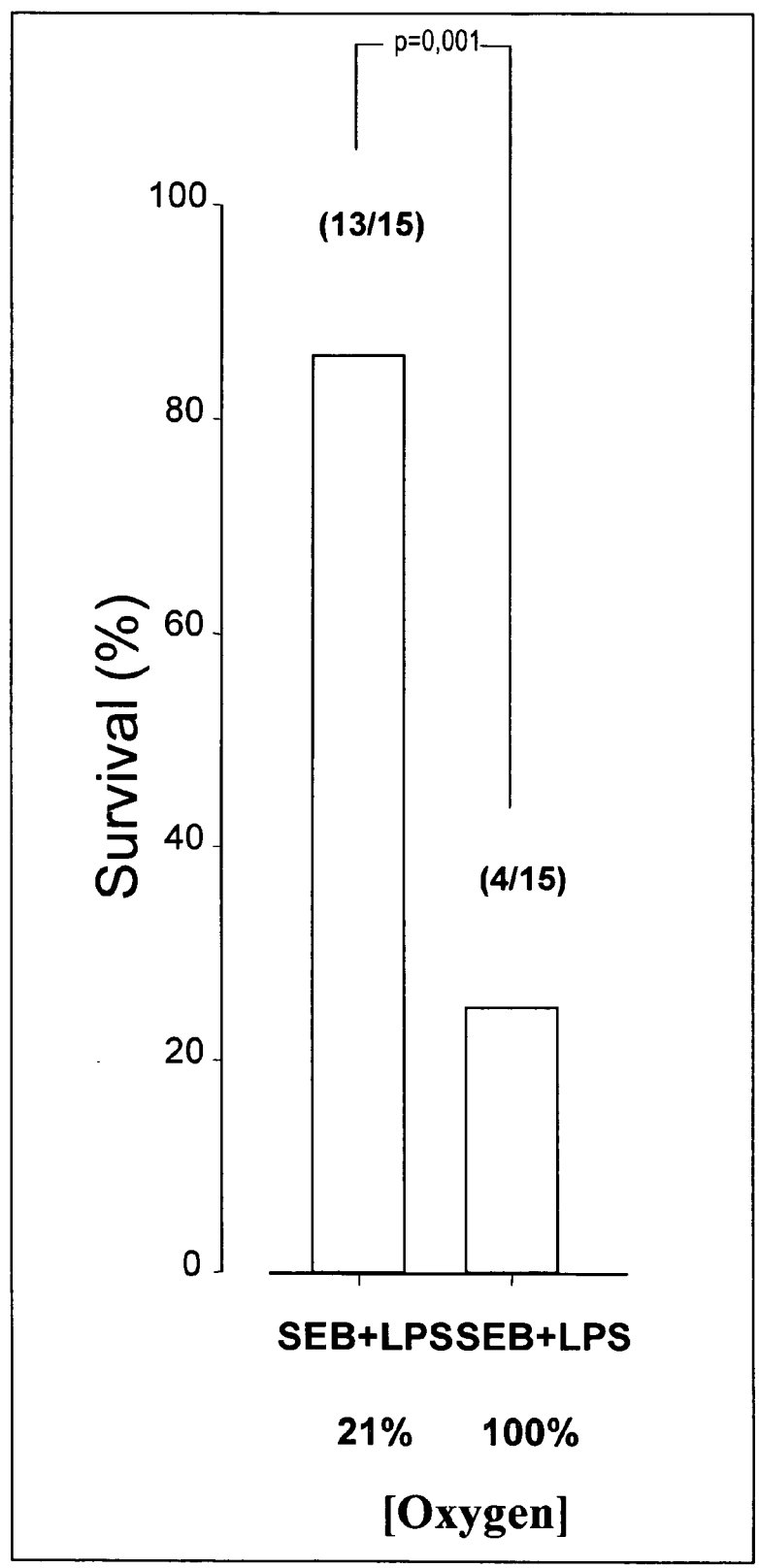
FIG. 1 depicts the increased death rate upon oxygenation of mice with acute inflammatory lung injury.

The Applicants has discovered that oxygen therapy exacerbates an ongoing inflammatory response and increases tissue damage by activated immune cells, that is, that oxygen has pro-inflammatory effects if administered during an ongoing inflammation process. These pro-inflammatory effects of oxygen are seen in conditions when an at-risk subject receives an increased amount of oxygen while suffering ongoing inflammatory conditions. The invention provides a method to avoid further, iatrogenic disease and/or deterioration of such conditions.

This invention screens for and identifies at-risk subject so that they do not suffer from pro-inflammatory properties of oxygen. The invention provides a method to identify the population of subjects who are most likely to suffer adverse effects of increased amount of oxygen (at-risk subjects) and pre-treating such subjects so as to minimize or eliminate the pro-inflammatory effects. "At-risk subjects" are those subjects who suffer from inflammatory diseases before any introduction to increased amounts of oxygen. Increased amounts of oxygen are understood to mean levels greater than the ambient amount of oxygen. Such increases in amounts of oxygen in accordance with the methods of the invention are, for example, a result of both therapeutic and recreational use of hyperbaric apparatus.

In one embodiment, the invention provides a method to decrease the risk of iatrogenic conditions. In one embodiment, the method of the invention provides for the administration of oxygen therapy without the attendant exacerbation of inflammation. In one preferred embodiment, the at-risk subject is administered an increased amount of oxygen by inhalation. In another preferred embodiment, the at-risk subject is an administered an increased amount of oxygen by placing the subject in a suitable chamber or room with levels of oxygen being higher than ambient levels. In another preferred embodiment, the at-risk subject is administered an increased amount of oxygen by placing the subject in a suitable hyperbaric chamber with levels of oxygen being higher than ambient level. In yet another embodiment, an increased amount of oxygen is administered to an at-risk subject by injecting the subject intravenously with oxygen-saturated blood or blood products, including synthetic blood components.

As such, the invention relates to methods of treatment, prevention or diagnosis of conditions due to the immune response, inflammation and tissue damage by prophylactically administering an anti-inflammatory compound. While not wishing to be held to a single theory, it is believed that the administration of an anti-inflammatory prior to the administration of increased amounts of oxygen halts oxygen's interruption of the physiological anti-inflammatory mechanism in vivo. That is, the anti-inflammatory mechanism is triggered by, and dependent upon the lack of oxygen, i.e. it is anaerobic. Thus, the pre-emptive administration of the anti-inflammatory agent minimizes or eliminates the adverse effect of premature termination of the natural activities of immune cells. Still further, the invention also provides for enhanced treatment, prevention and diagnosis of pathogenic diseases. For example, again while not wishing to be bound to a single theory, in at-risk patients the survival of a pathogen (for example, bacteria and viruses) due to the insufficient, short-lived and/or prematurely terminated activities of immune cells such as that in oxygen therapy causes the pathogenic disease to become entrenched, renewed or more dangerous.

Although counter-intuitive, Applicants discovered that the administration of oxygen further exacerbates lung injury in mice with inflamed lungs in conditions modeling the polymicrobial infection and sepsis. Mice which were exposed to oxygen in conditions mimicking treatment of patients with lung diseases dramatically increased levels of pro-inflammatory cytokines and inflammation. Still further, this was accompanied by a strong increase and increase in inflammatory lung tissue damage and resulted in much accelerated death.

This discovery is completely different from the state-of the art views, where oxygen was considered to have some toxic effects because of reactive oxygen species. In fact, the toxic effects, if any, of reactive oxygen species is not the key. Treatments aimed at countering the same by reducing reactive oxygen species have not been widely successful. Applicants' discovery changes the focus of treatment to allowing the tissue-protecting anti-inflammatory hypoxia and the positive pro-inflammatory effects of activated immune cells.

The Applicants has also discovered the method to prevent these grave side-effects of otherwise life-saving oxygen. The invention provides methods of prevention of iatrogenic complication of the widely used clinical procedure of oxygen therapy. As used herein the term "iatrogenic" disease is now applied to any adverse effect associated with any treatment or medical practitioner. The administration of exogenous anti-inflammatory agents prior to the introduction of increased amount of oxygen, be it in recreational or medicinal use of oxygen, can prevent of minimize the unwanted side effects of such introduction of oxygen. For example, in the field of oxygen therapy, often gas mixtures containing greater than 15%, for example 20 or 21% are administered to subjects in need thereof. Indeed, using amounts greater than 15%, for example about 21% oxygen can be dangerous. Subjects may receive the increased amounts of oxygen through spontaneous breathing, inspiration by mechanical ventilation, and by infusion of blood or solution with increased levels of oxygen. For example, a patient with inflamed organs may receive a transfusion or administered an i.v. containing elevated oxygen levels. It has been discovered that such a course of treatment, without more, can cause unintended harm to the patient and indeed, put the patient at higher risk then if not treatment at all were given.

As will be described further, the treatment of lung-inflamed mice with both oxygen and with an anti-inflammatory compound resulted in complete prevention of the oxygen treatment-associated exacerbation of lung inflammation and rescue of mice from inflammation and from the oxygen therapy-induced death. Without being bound to a single theory, it is believed that treatment compensates for the oxygen-induced loss of the endogenous anti-inflammatory pathway.

In one embodiment, the application of an anti-inflammatory compound resulted in dramatically decreased levels of pro-inflammatory cytokines, decreased tissue damage and rescued mice from death. Applicants have discovered that the promotion of the anti-inflammatory events during the oxygen treatment of inflamed patients maintains high oxygen tension in lungs and prevents the exacerbation of inflammatory tissue damage. For example, the inflamed lung of an asthmatic will likely worsen with oxygen treatment, not improve, in the absence of the invention.

For example, in one embodiment, an application of anti-inflammatory compound A2A receptor agonist decreased levels of pro-inflammatory cytokines, decreased tissue damage and rescued mice from death.

These data provided the in vivo demonstrate that combining oxygen therapy with the targeted activation of A2 receptor or with another anti-inflammatory drug represents a novel method of safe oxygen therapy in conditions of ongoing inflammation. These data also provided a proof of principle that similar approach can be used to improve oxygen therapy during the treatment of other diseases with an inflammatory compound.

The present invention provides methods to prevent the oxygen-facilitated inflammatory tissue injury and thereby improve the widely used in clinic therapeutic procedure.

The method of the invention involves administering compounds capable of activating expression and functions of A2 adenosine receptor, increasing A2 receptor gene expression or preventing the A2 receptor degradation in order to recruit anti-inflammatory signaling trough A2 receptor in order to prevent tissue damage by oxygen therapy.

In one embodiment, the method of the invention involves the administration of synthetic or natural compounds that have properties of anti-inflammatory agents, that interfere with recognition and/or signaling and/or effector functions such as, but not limited to, the secretion of cytotoxic pro-inflammatory molecules, including cytokine, reactive oxygen species and mediators of other anti-inflammatory pathways.

In other embodiments, the method of the invention involves synthetic or natural compounds that have properties of activators or stabilizers of A2 adenosine receptors and/or their signaling pathways.

In certain aspects, the methods of the invention decrease an immune response, inflammation and thereby accomplish protection from the oxygen-induced tissue damage by administering either an inhibitor of pro-inflammatory pathway or bioactive agent (e.g. small interfering RNA (siRNA) or ribozyme) that destroys pro-inflammatory molecules expression or bioactive agents that stabilize expression of anti-inflammatory molecules. In one embodiment, the bioactive agent acts on A2 adenosine receptors.

Suitable compounds (bioactive agents) for use in the invention include but are not limited to i) inhibitors of transmembrane signaling pathways in cells of innate immune system, for example myeloid cells or cells of adaptive immune system such as T cells; ii) activators of cAMP-mediated immunosuppressive pathways. iii) Inhibitors of cAMP-degradation pathways e.g. inhibitors of cAMP phosphodiesterase such as rollipram. In one embodiment, agonists of Gs protein coupled receptors (e.g. beta adrenergic, histamine receptors) are used.

Non-steroid anti-inflammatory drugs are suitable compounds for use in the instant invention and include, Naproxen (such as Aleve, Naprosyn), Sulindac (such as Clinoril), Tolmetin (such as Tolectin), Ketorolac (such as Toradol), Celecoxib (such as Celebrex), ibuprofen (such as Advil, Motrin, Medipren, Nuprin), diclofenac (such as Voltaren, Cataflam, Voltaren-XR), acetylsalicylic acid (such as Aspirin, Ecotrin), nabumetone (such as Relafen), etodolac (such as Lodine), indomethacin (such as Indocin, Indocin-SR), piroxicam (such as Feldene), Cox-2 Inhibitors, ketoprofen (Orudis, Oruvail), Antiplatelet Medications, salsalate (such as Disalcid, Salflex), valdecoxib (such as Bextra), oxaprozin (Daypro), diflunisal (such as Dolobid) and flurbiprofen (such as Ansaid). It is understood that derivatives of the above such as salts, polymorphs and the like are suitable for use in the invention.

Other suitable bioactive agents include anti-inflammatory agents based on the use of corticosteroids and leukotrienes are suitable. These include, but are not limited to, oral (and intravenous) corticosteroids (systemic corticosteroids), inhaled corticosteroids, leukotriene modifiers (Accolate and Singular). Suitable examples of oral or intravenous corticosteroids include, but are not limited to Cortisone, Hydrocortisone (such as Cortef®), Prednisone (such as Deltasone®, Meticorten®, Orasone®), Prednisolone (such as Delta-Cortef®, Pediapred®, Prelone®), Triamcinolone (such as Aristocort®, Kenacort®), Methylprednisolone (such as Medrol, Methylpred, Solu-Medrol), Dexamethasone (such as Decadron®, Dexone®, Hexadrol®), Betamethasone (such as Celestone®) and the like.

Suitable inhaled corticosteroids include but are not limited to Beclomethasone (such as Beclovent®, Beconase®, Vanceril®, Vancenase®), Budesonide (such as Pulmicort®, Rhinocort®), Mometasone (such as Nasonex®), Triamcinolone (such as Azmacort®, Nasacort®), Flunisolide (such as Aero-Bid®, Nasalide®, Nasarel®), Fluticasone (such as Flovent®, Flonase®).

Other suitable anti-inflammatory agents include some commercially available agents such as Advair (a combination medication that includes a corticosteroid plus a long acting bronchodilator drug), Aerobid, Azmacort, Flovent, Pulmicort, Qvar and the like. As know to those of skill in the art, inhaled corticosteroids can be administered via at least three forms, for example, the metered dose inhaler (MDI), dry powder inhaler (DPI) and nebulizer solutions. Such mode of administration are suitable in the practice of the invention.

Still other suitable examples include leukotriene modifiers such as but not limited to Accolate, Singulair, Zyflo and the like.

By mitigating the activating anti-inflammatory pathways to prevent or minimize the pro-inflammatory effects of oxygen, in particular by the combined use of oxygen and anti-inflammatory drugs, Applicants provides potentially life saving procedures for critically ill patients.

In yet another aspect the invention includes a method for treating a disease which could be alleviated by the decrease in an adenosine kinase activity in a subject in need of such treatment, comprising administering to the subject an adenosine kinase inhibitor or bioactive agent, for example, small interfering RNA (siRNA) that destroys adenosine kinase expression or bioactive agent that prevents degradation of adenosine kinase.

Disclosed are methods for treating a disease associated with an oxygen therapy in a subject in need of such treatment, comprising administering to the subject an anti-inflammatory compound such that adverse effects of the oxygen therapy are minimized or eliminated.

In still another aspect, a method for treating a disease associated with an oxygen therapy in a subject in need of such treatment is disclosed wherein disease is associated with interruption of the local blood supply and/or decrease of local oxygen tension and/or disregulation of cell metabolism.

The methods of the invention are employed in the treatment of inflammatory responses due to organ, tissue or cell transplantation, for example, the transplantation of allogenic or xenogenic tissue into a mammalian recipient, joint replacement, autoimmune diseases and inflammatory conditions due to circulatory pathologies and the treatment thereof, including angioplasty, stent placement, shunt placement or grafting with the pathology or trauma that initiates the inflammatory response.

Unless explained otherwise, all technical and scientific terms used herein have the same meaning as commonly understood to one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Methods and materials similar or equivalent to those described herein can be used in the practice or testing of the present disclosure. The materials, methods, and examples are illustrative only and not intended to be limiting.

Hypoxia: The state in which oxygen demand exceeds supply.

Adjuvant: Any agent that enhances or increases one or more immune-stimulating properties of another agent (such as a chemical compound or antigenic epitope). An adjuvant augments, stimulates, activates, potentiates, or modulates the immune response at the cellular or humoral level.

For example, addition of an adjuvant to a vaccine improves the immune response of a cell, such as a cell in a subject. An adjuvant can be used so that less vaccine is needed to produce the immune response. One specific, non-limiting example of an adjuvant is Freund's adjuvant, which is a water-in-oil emulsion that contains an immunogen, an emulsifying agent and mycobacteria. The classical agents (Freund's adjuvant, BCG, *Corynebacterium parvum*) contain bacterial antigens. Some adjuvants are endogenous (e.g. histamine, interferon, transfer factor, tuftsin, interleukin-1 and interleukin-12). The mode of action of an adjuvant can be non-specific, resulting in increased immune responsiveness to a wide variety of antigens, or antigen-specific, i.e. affecting a restricted type of immune response to a narrow group of antigens. The therapeutic efficacy of many biological response modifiers is related to their antigen-specific immunoadjuvanticity.

Agent: Any polypeptide, compound, small molecule, organic compound, salt, polynucleotide, peptidomimetic, or other molecule of interest.

Animal: Living multi-cellular vertebrate organisms, a category that includes, for example, mammals and birds. The term mammal includes both human and non-human mammals. Similarly, the term "subject" includes both human and veterinary subjects.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T). Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Antisense oligonucleotide: A sequence of at least about 8 nucleotides, such as about at least 10, 12, 15, 20, 30 or 50 nucleotides, wherein the sequence is from a gene sequence (such as all or a portion of a cDNA or gene sequence, or the reverse complement thereof), arranged in reverse orientation relative to the promoter sequence in a transformation vector.

Autoimmune disorder: A disorder in which the immune system produces an immune response (e.g. a B cell or a T cell response) against an endogenous antigen, with consequent injury to tissues.

Biological samples: Suitable biological samples include samples containing genomic DNA, RNA (including mRNA), and/or protein, obtained from cells of a subject. Examples include, but are not limited to, peripheral blood, urine, semen, saliva, tissue biopsy, surgical specimen, amniocentesis samples, derivatives and fractions of blood such as serum, and biopsy material.

Cancer: Malignant neoplasm that has undergone characteristic anaplasia with loss of differentiation, increase rate of growth, invasion of surrounding tissue, and is capable of metastasis.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Comprises; A term that means "including." For example, "comprising A or B" means including A or B, or both A and B, unless clearly indicated otherwise.

Cytokine: Proteins made by cells that affect the behavior of other cells, such as lymphocytes. In one embodiment, a cytokine is a chemokine, a molecule that affects cellular trafficking.

DNA: Deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Deletion: The removal of a sequence of DNA, the regions on either side being joined together.

Differentiation: The process by which cells become more specialized to perform biological functions. Differentiation is a property that is totally or partially lost by cells that have undergone malignant transformation.

Epitope: An antigenic determinant. These are particular chemical groups or peptide sequences on a molecule that are antigenic, i.e. that elicit a specific immune response. An antibody binds a particular antigenic epitope.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Hypersensitivity: Immune responses to innocuous antigens that lead to symptomatic reactions upon re-exposure are called hypersensitivity reactions. These can cause hypersensitivity diseases if they occur repetitively. This state of heightened reactivity to an antigen is called hypersensitivity. Hypersensitivity reactions are classified by mechanism: type I hypersensitivity reactions involve IgE antibody triggering of mast cells; type II hypersensitivity reactions involve IgG antibodies against cell-surface or matrix antigens; type III hypersensitivity reactions involve antigen:antibody complexes; and type iV hypersensitivity reactions are T cell-mediated.

Immune cell: Any cell involved in a host defense mechanism, such as cells that produces pro-inflammatory cytokines, and such as cells that participate in tissue damage and/or disease pathogenesis. Examples include, but are not limited to: T cells, B cells, natural killer cells, neutrophils, mast cells, macrophages, antigen-presenting cells, basophils, and eosinophils.

Immune response: A response of a cell of the immune system, such as a B cell or T cell, to a stimulus. In one embodiment, the response is specific for a particular antigen (an "antigen-specific response"). In one embodiment, an immune response is a T cell response, such as a Th1, Th2, or Th3 response.

Inflammation: When damage to tissue occurs, the body's response to the damage is usually inflammation. The damage can be due to trauma, lack of blood supply, hemorrhage, autoimmune attack, transplanted exogenous tissue or infection. This generalized response by the body includes the release of many components of the immune system (e.g. IL-1 and TNF), attraction of cells to the site of the damage, swelling of tissue due to the release of fluid and other processes.

Inflammation, the response of tissue to injury, is divided into two phases, termed acute and chronic. In the acute phase, inflammation is characterized by increased blood flow and vascular permeability, accumulation of fluid, and accumulation of leukocytes and inflammatory mediators (e.g. cytokines). In the subacute/chronic phase, inflammation is characterized by the development of specific humoral and cellular immune responses to the pathogen(s) present at the site of tissue injury. During both the acute and chronic inflammatory processes, a variety of soluble factors are involved in leukocyte recruitment through increased expression of cellular adhesion molecules and chemoattraction. Many of these soluble mediators regulate the activation of both the resident cells (such as fibroblasts, endothelial cells, tissue macrophages, and mast cells) and newly recruited inflammatory cells (such as monocytes, lymphocytes, neutrophils, and eosinophils).

Leukocyte: Cells in the blood, also termed "white cells," that are involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B-cells and T-cells.

Mammal: This term includes both human and non-human mammals. Similarly, the term "subject" includes both human and veterinary subjects.

Monoclonal antibody: An antibody produced by a single clone of B-lymphocytes. Monoclonal antibodies are produced by methods known to those of skill in the art, for instance by making hybrid antibody-forming cells from a fusion of myeloma cells with immune spleen cells.

Natural killer (NK) cell: These are large, usually granular, non-T, non-B lymphocytes, which kill certain tumor cells. NK cells are important in innate immunity to viruses and other intracellular pathogens, as well as in antibody-dependent cell-mediated cytotoxicity (ADCC).

Neoplasm: An abnormal mass of tissue that results from excessive cell division hat is uncontrolled and progressive, also called a tumor. Neoplasms can be begin (neither infiltrative nor cancerous) or malignant (invasive).

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA or RNA) which is at least 6 nucleotides, for example at least 15, 25, 50, 75, 100 or even 200 nucleotides long.

Pharmaceutical agent: A chemical compound or composition capable of inducing a desired therapeutic or prophylactic effect when properly administered to a subject or a cell. "Incubating" includes a sufficient amount of time for an agent to interact with a cell. "Contacting" includes incubating an agent in solid or in liquid form with a cell.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of adenosine receptor modulators.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any chain of amino acids, regardless of length or post-translational modification (e.g. glycosylation or phosphorylation).

Preventing or treating a disease: "Preventing" a disease refers to inhibiting or decreasing the full development of a disease, for example in a person who is known to have a predisposition to a disease. An example of a person with a known predisposition is someone with a history of diabetes in the family, or who has been exposed to factors that predispose the subject to a condition, such as lupus or rheumatoid arthritis. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide or nucleic acid preparation is one in which the peptide or nucleic acid is more enriched than the peptide or nucleic acid is in its natural environment within a cell. Preferably, a preparation is purified such that the protein or nucleic acid represents at least 50% of the total peptide or nucleic acid content of the preparation.

Receptor: A molecular structure within a cell or on the surface of a cell, characterized by selective binding of a specific substance and a specific physiological effect that accompanies the binding, for example, cell surface receptors for peptide hormones, neurotransmitters, immunoglobulins, small molecules, and cytoplasmic receptors for steroid hormones. An adenosine receptor is a cell surface receptor for adenosine, and includes, but is not limited to, the A2 or A3 receptors.

Ribozyme: Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs can be used to confer RNA cleaving activity on the antisense RNA, such that endogenous mRNA molecules that bind to the antisense RNA are cleaved, which in turn leads to an enhanced antisense inhibition of endogenous gene expression.

Specific binding agent: An agent that binds substantially only to a defined target. Thus an antibody or antibody fragment-specific binding agent binds substantially only the defined antibody or antibody fragment, or an antibody region within a protein, such as a fusion protein. As used herein, the term "adenosine receptor specific binding agent," includes anti-adenosine receptor antibodies (and functional antibody fragments thereof) and other agents (such as potential therapeutic agents) that bind substantially only to adenosine receptors.

Antibodies can be produced using standard molecular procedures described in a number of texts, including Harlow and Lane (*Antibodies, A Laboratory Manual*, CSHL, New York, 1988). The determination that a particular agent binds substantially only to the target protein or peptide can readily be made by using or adapting routine procedures. One suitable in vitro assay makes use of the Western blotting procedure (Harlow and Lane, *Antibodies, A Laboratory Manual*, CSHL, New York, 1988).

Shorter fragments of antibodies can also serve as specific binding agents. For instance, FAbs, Fvs, and single-chain Fvs (SCFvs) that bind to adenosine receptor would be adenosine receptor-specific binding agents.

Subject: Living multi-cellular vertebrate organisms, a category that includes both human and non-human mammals.

T Cell; A white blood cell involved in the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte. In another embodiment, a CD8 cell is a suppressor T cell.

Target sequence: A portion of ssDNA, dsDNA or RNA that, upon hybridization to a therapeutically effective oligonucleotide or oligonucleotide analog, results in the inhibition of gene expression, such as adenosine receptor gene expression. An antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Therapeutically effective amount: A quantity of an agent or composition sufficient to achieve a desired effect in a subject being treated. For instance, this can be the amount necessary to increase activity of an immune cell and/or enhance an immune response in a subject. In one example, it is an amount that will inhibit viral, fungal, or bacterial replication or to measurably alter outward symptoms of the viral, fungal, or bacterial infection. In another example, it is an amount that will decrease or prevent further tumor growth. When administered to a subject, a dosage will generally be used that will achieve target tissue concentrations (for example, in lymphocytes) that has been shown to achieve in vitro inhibition of viral replication or reduction of tumor cells.

Therapeutically effective dose: A dose sufficient to prevent advancement, or to cause regression of the disease, for example a dose sufficient to reduce the volume or size of a tumor. In another example, it is an amount which is capable of relieving symptoms caused by a disease, such as pain or swelling.

Therapeutically effective adenosine receptor oligonucleotides and oligonucleotide analogs: Characterized by their ability to inhibit or decrease expression of adenosine receptors. As described below, complete inhibition is not necessary for therapeutic effectiveness. Therapeutically effective oligonucleotides are characterized by their ability to inhibit or decrease the expression of adenosine receptors. Inhibition is a reduction in adenosine receptor expression observed when compared to adenosine receptor production in the absence of the oligonucleotide or oligonucleotide analog. For example, an oligonucleotides may be capable of inhibiting the expression of adenosine receptors by at least 15%, 30%, 40%, 50%, 60%, or 70%, or more, and still be considered to be effective.

Effective amounts of oligonucleotides and oligonucleotide analogs are additionally characterized by being sufficiently complementary to adenosine receptor-encoding nucleic acid sequences. As described herein, sufficient complementary means that an effective oligonucleotide or oligonucleotide analog can specifically disrupt the expression of adenosine receptors, and not significantly alter the expression of genes other than adenosine receptors.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Treatment: Refers to both prophylactic inhibition of initial infection, and therapeutic interventions to alter the natural course of an untreated disease process, such as infection with a virus.

Tumor: An abnormal mass of tissue that results from excessive cell division that is uncontrolled and progressive, also called a neoplasm. Tumors can be benign (neither infiltrative nor cancerous) or malignant (invasive).

Vaccine: A dead or attenuated (non-pathogenic) form of a pathogen, or an antigen isolated from a pathogen, administered to a subject to induce adaptive immunity to the pathogen.

Vector: A nucleic acid molecule as introduced into a host cell, thereby producing a transformed host cell. A vector can include nucleic acid sequences that permit it to replicate in the host cell, such as an origin of replication. A vector can also include one or more selectable marker genes and other genetic elements known in the art. The term "vector" includes viral vectors, such as adenoviruses, adeno-associated viruses, vaccinia, and retroviruses vectors.

It will be appreciated by those skilled in the art that the conclusions reached in studies of polymicrobial infections and sepsis model reach beyond this particular model to include the pathogenesis of other major diseases with an inflammatory compound. It will be understood that the particular embodiments of the invention are shown by way of illustration and not as limitations of the invention. The principle features of this invention can be employed in various embodiments without departing from the scope of the invention.

The present invention pertains to methods of oxygen therapy in a mammal with ongoing inflammatory diseases. The methods include administration of a therapeutically effective amount of bioactive agent that prevents exacerbation of inflammation and tissue damage. The invention provides methods of treatment of patients requiring oxygen therapy by decreasing side effects of oxygen.

The need to maintain anti-inflammatory pathway during oxygen therapy is new as prior to the present invention, this major clinical procedure (oxygen administration) is not considered to be pro-inflammatory. Yet such administration is the very definition of an iatrogenic disease (medically cure-induced disease). In the practice of the invention iatrogenic disease is prevented.

Inflamed local tissue environments are hypoxic and the tissue damage-associated hypoxia is conducive to accumulation of elevated levels of extracellular adenosine. The recently provided genetic evidence for the critical role of extracellular adenosine and of Gs protein coupled A2A adenosine receptors in down-regulation of activated immune cells in vivo (Ohta A and Sitkovsky M. Role of G-protein-coupled adenosine receptors in downregulation of inflammation and protection from tissue damage. *Nature*, 414: 916-920, 2001) suggested that inflammation-induced local tissue damage-associated hypoxia and oxygen sensors may serve as primary signals of excessive tissue damage in order to de-activate immune cells.

Many clinical conditions, including aspiration, trauma, and hemorrhagic shock are frequently followed by pulmonary and systemic infectious and septic complications that lead to pulmonary dysfunction and subsequent lung failure. For example, the acute lung injury (ALI) or its more severe form, the Acute Respiratory Distress Syndrome (ARDS) occur with a frequency of approximately 130,000 cases and more than 50,000 deaths from ARDS per year only in the USA.

Intubation and mechanical ventilation represent one of the most widely used prophylactic and therapeutic clinical interventions to counteract the insufficient pulmonary oxygen-delivering capacity of these patients who suffer from severe lung inflammation. Although the majority of patients respond well to oxygen therapy with oxygen toxicity being an uncommon occurrence in intensive care medicine, there still remains the possibility that oxygen therapy may be suboptimal in ARDS patients as it may promote deleterious pulmonary inflammation, which fuels this disease process. Since the magnitude and duration of lung inflammation was shown to determine the final outcome of ARDS patients, it is important to carefully evaluate the possible adverse effects of oxygen on inflammatory processes.

Applicants hypothesized that exposure to oxygen in conditions mimicking those with patients undergoing oxygen therapy would increase an ongoing inflammation and exacerbate inflammatory tissue damage in vivo. They predicted that it would affect the course of disease in a clinically relevant model of bacterial infection and sepsis. To enable this investigation, Applicants adapted a murine model of polymicrobial lung infection.

The Applicants subjected mice to combined inhalation of toxins from gram-positive and gram-negative bacteria. In this model of polymicrobial lung infection intratracheal (i.t.) injection of both lipopolysacharide (LPS) and *Staphylococcus* enterotoxin B (SEB) strongly potentiates their toxicity. These assays confirmed the prediction of exaggerated lung injury in mice in conditions that mimic therapeutic oxygenation and this is reflected in the dramatic increases in inflammatory lung damage in different in vivo and ex vivo assays. The results revealed a heretofor unappreciated pro-inflammatory effects of oxygen therapy, which exacerbate the lung tissue damage and the disease pathogenesis. The Applicants found therapeutic countermeasures to this iatrogenic complication by combining oxygen therapy with the use of anti-inflammatory agents.

EXAMPLES

Example 1

FIG. 1

The death rate increased upon oxygenation of mice with acute inflammatory lung injury. Mice were intratracheally (i.t.) injected with SEB and LPS to model polymicrobial infection and were exposed to 21% or 100% oxygen for 48-60 h. Determination of time-dependent survival curves was prohibited by considerations of unrelieved severe respiratory distress, which required termination of experiments immediately after differences between groups became apparent. Major differences between groups occurred within 48-60 hours after intratracheal injection of toxins, when the majority of oxygenated animals with inflamed lungs had died, while the non-oxygenated and obviously sick control mice with inflamed lungs were still alive.

Figure 2A:
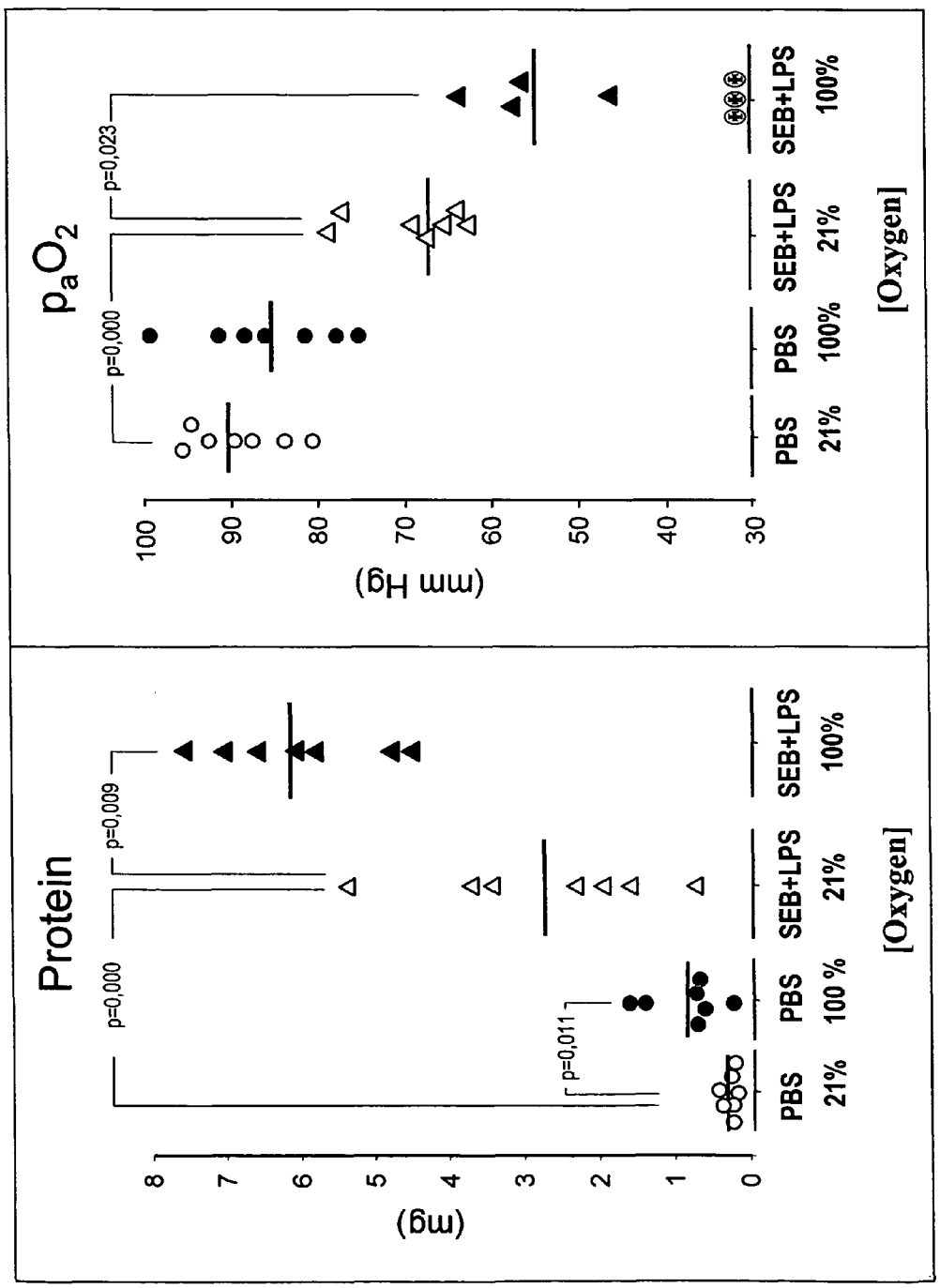
FIGS. 2A&B depict exacerbation of inflammatory lung injury after exposure of mice to 100% or 60% oxygen-containing gas mixture as compared to ambient 21% oxygen containing atmosphere.

Five times more mice with inflamed lungs died after exposure to 100% oxygen than were observed among control mice with inflamed lungs, which were left at 21% ambient oxygen tension (FIG. 1). This was further confirmed by a much more pronounced increase in the alveolo-capillary permeability, and severe overall impairment of lung gas exchange as evidenced by the increase in the amount of protein recovered from the alveolar space by broncho-alveolar lavage (BAL) as well as by the decrease in arterial $pO^2$ values of previously oxygen-exposed mice when returned back to normal atmosphere (FIG. 2A). Although exposure of mice to 100% oxygen alone (with no toxin inhalation) did induce small accumulation of BAL fluid protein, the magnitude of that effect could not account for the observation of dramatic increases in lung vascular permeability and impairment of lung gas exchange when both toxins and oxygenation were used (FIG. 2A).

Figure 2B:
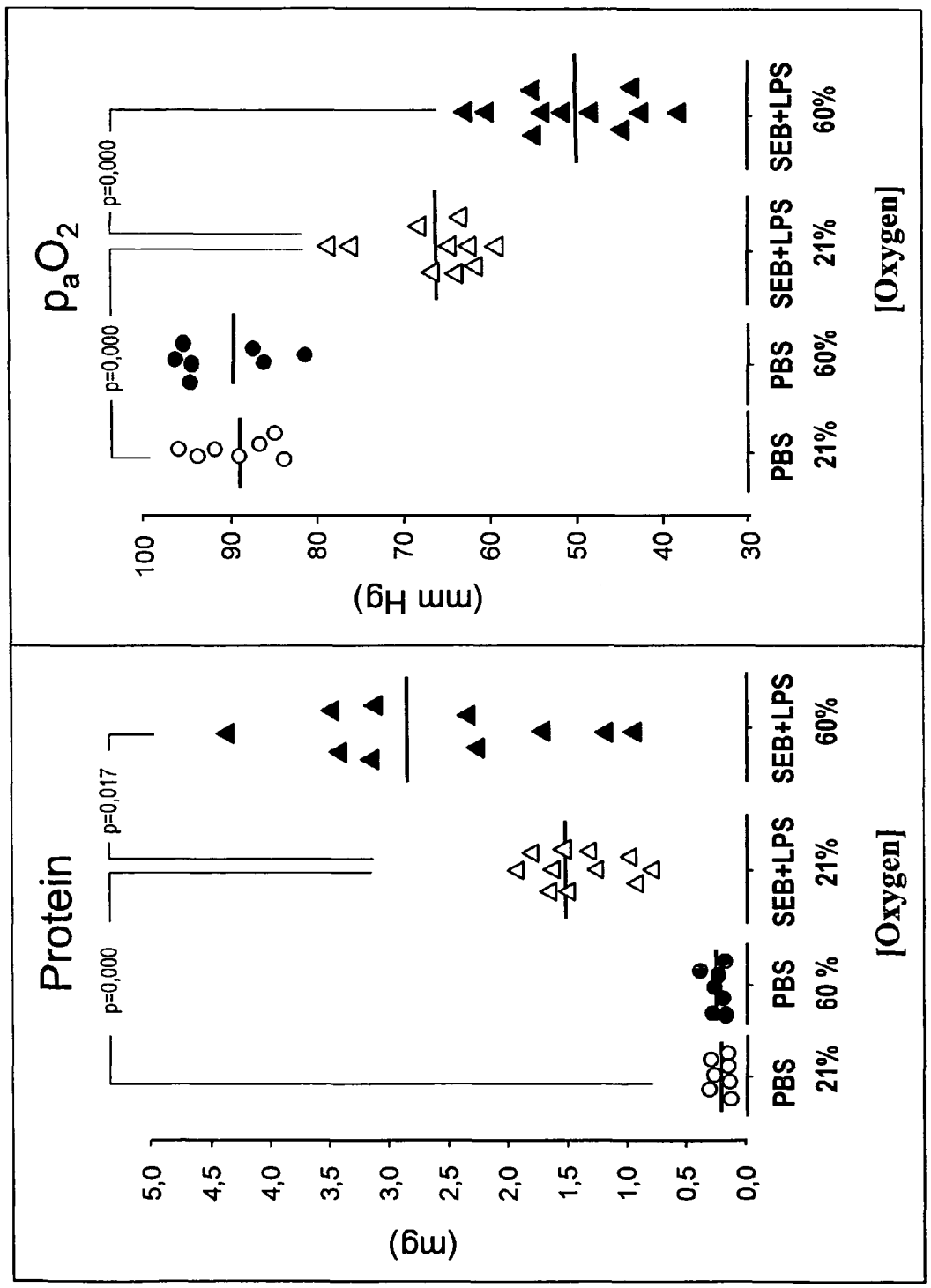

The exacerbation of inflammatory lung injury was also observed when mice were exposed to 60% oxygen, a concentration considered in patients as fairly safe, as compared with the animals breathing 21% oxygen and this is reflected in accumulation of exudates protein in the alveolar spaces and impaired arterial blood oxygen tensions (FIG. 2B). Exposure of toxin-injected mice to 60% oxygen, however, did not result in death in used short-term assays.

These observations confirmed the prediction of exacerbation of inflamed lung injury by oxygenation, but the development of therapeutic countermeasures requires testing of the validity of our underlying assumptions and conclusive identification of the molecular mechanisms of these pro-inflammatory effects of oxygen.

The observed effects of oxygenation could not be accounted for by direct toxic effects of oxygen, since these effects of oxygen take much longer to manifest and therefore are unlikely to fully account for the dramatic lung injury observed in these short-term experiments (FIGS. 1, 2A, B).

Example 2

(FIG. 2) The exacerbation of inflammatory lung injury after exposure of mice to 100% or 60% oxygen-containing gas mixture as compared to ambient 21% oxygen containing atmosphere.

2A) Enhanced lung vascular permeability and impairment of lung gas exchange in mice breathing 100% $O_2$ upon induction of acute lung injury. Following intratracheal injection of mice with SEB and LPS, animals were breathing 21% or 100% oxygen. Forty eight hours later, lung vascular permeability and lung gas exchange were determined by the amount of protein recovered by bronchoalveolar lavage or by measuring $pO_2$ values in arterial blood drawn 15 min after return of mice to normal atmosphere. During this equilibration period three out of seven mice previously exposed to 100% oxygen died, so that no arterial blood gas analyses could be performed, but BAL protein concentrations were determined immediately thereafter.

2B) Increased lung vascular permeability and impairment of lung gas exchange in mice with acute lung injury even upon exposure to lower levels of oxygen (60%), which are considered clinically safe. Experimental conditions were the same as under A) except oxygen concentration was 60%.

A much more pronounced increase in the alveolo-capillary permeability, and severe overall impairment of lung gas exchange was evidenced by the increase in the amount of protein recovered from the alveolar space by broncho-alveolar lavage (BAL) as well as by the decrease in arterial $pO_2$ values of previously oxygen-exposed mice when returned back to normal atmosphere (FIG. 2A). Although exposure of mice to 100% oxygen alone (with no toxin inhalation) did induce small accumulation of BAL fluid protein, the magnitude of that effect could not account for the observation of dramatic increases in lung vascular permeability and impairment of lung gas exchange when both toxins and oxygenation were used (FIG. 2A).

The exacerbation of inflammatory lung injury was also observed when mice were exposed to 60% oxygen, a concentration considered in patients as fairly safe, as compared with the animals breathing 21% oxygen and this is reflected in accumulation of exudates protein in the alveolar spaces and impaired arterial blood oxygen tensions (FIG. 2B). Exposure of toxin-injected mice to 60% oxygen, however, did not result in death in used short-term assays.

Example 3

(FIG. 3) Intratracheal administration of anti-inflammatory drug protects from increased death rate upon oxygenation of mice with acute lung injury thereby providing new method of oxygen therapy without pro-inflammatory side effects. Method of In vivo administration of anti-inflammatory drug: The anti-inflammatory $A_{2A}$ receptor agonist CGS21680 was dissolved in PBS and administered by intratracheal injection at 0.1 mg/kg b.w. in a total volume of 50 μl per mouse. Intratracheal injection of CGS21680 was repeated every 8 h until termination of the experiment. In control animals, the solvent of CGS21680, i.e. PBS only was administered. CGS21680 solution or solvent were injected within 15 min after administration of either SEB or LPS in both models of lung injury, respectively.

Figure 3:
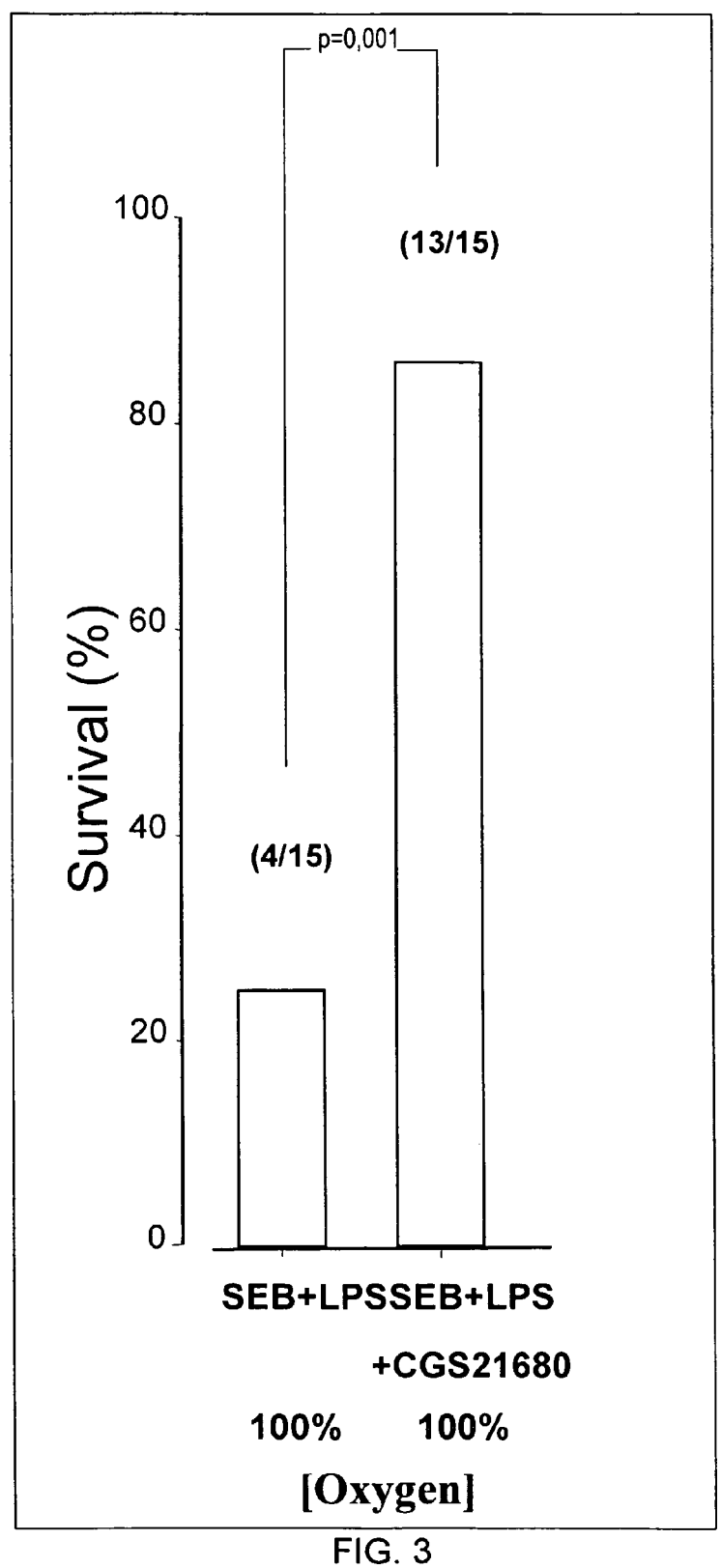
FIG. 3 depicts intratracheal administration of anti-inflammatory drug that protects from increased death rate upon oxygenation of mice with acute lung injury.

Treatment with the $A_{2A}R$ selective agonist CGS21680 was effective even when applied in the more severe polymicrobial toxin model of lung injury and i.t. injections of this agonist under hyperoxic conditions rescued the majority of mice from oxygenation-induced death. The death rate was 80% among oxygenated mice with inflammatory lung injury in the control group, but the number of deaths was dramatically reduced among the $A_{2A}R$ agonist treated oxygenated animals (FIG. 3).

It was found (data not shown) that i.t. injections of the selective $A_{2A}R$ agonist CGS21680 significantly inhibited lung injury in endotoxin-treated mice and led to i) significantly decreased accumulation of PMN, ii) reduced production of reactive oxygen metabolites, iii) less pronounced increases in lung vascular permeability, and iv) improved lung gas exchange. Histological examination of $A_{2A}R$ agonist-treated mice revealed that therapeutic effects of agonist CGS21680 was similar to that of exposure of mice to hypoxia. CGS21680 treatment resulted in inhibition of pulmonary PMN sequestration, and was followed by a significant reduction of lung tissue damage as assessed by the fourfold decrease in the lung injury score (not shown).

Thus, the exogenously added selective, synthetic $A_{2A}R$ agonist compensated for the loss of endogenously formed adenosine in oxygenated and inflamed lungs thereby decreasing lung injury and rescuing mice from death. In an important control, CGS21680 at the dosing regimen used to treat WT mice was proven to be selective since it did not affect lung inflammation in $A_{2A}R$ gene deficient mice (data not shown).

While this invention has been particularly shown and described with references to preferred embodiments thereof, it will be understood by those skilled in the art that various changes in form and details may be made therein without departing from the scope of the invention encompassed by the appended claims.

We claim:

1. A method for reducing or inhibiting the development of tissue damage in an at-risk subject in need of oxygen therapy comprising:
administering a therapeutically effective amount of an anti-inflammatory agent to the at-risk subject prior to oxygen therapy, wherein the oxygen therapy comprises administering to the at risk subject an increased amount of oxygen, wherein the tissue damage is reduced or the development of tissue damage is inhibited as compared to the tissue damage in the absence of said prior administration of the anti-inflammatory agent, and wherein the anti-inflammatory agent consists of an A2A adenosine receptor agonist.

2. The method of claim 1, wherein the increased amount of oxygen is administered by inhalation.

3. The method of claim 1, wherein the increased amount of oxygen is administered by placing patient in a chamber or room with levels of oxygen being higher then ambient.

4. The method of claim 1, wherein the increased amount of oxygen is administered by placing patient in a hyperbaric chamber or room with levels of oxygen being higher then ambient.

5. The method of claim 1, the increased amount of oxygen is administered by injecting the patient intravenously with oxygen-saturated blood or blood products, including synthetic blood components.

6. The method of claim 1, wherein the at-risk subject is in a state of active inflammation.

7. The method of claim 6, wherein the at-risk subject has a condition normally responsive to increased oxygen levels in the absence of said of active inflammation.

8. The method of claim 1, wherein the tissue damage in the at-risk subject is inflammatory lung injury or ischemia-reperfusion induced inflammatory tissue injury.

9. A method for reducing or inhibiting the development of inflammatory lung injury associated with oxygen therapy in an at-risk subject in need of oxygen therapy comprising: administering a therapeutically effective amount of an anti-inflammatory agent to the at-risk subject prior to oxygen therapy, wherein the oxygen therapy comprises administering an increased amount of oxygen to the at-risk subject, wherein the inflammatory lung injury in the subject is reduced or the development of the inflammatory lung injury is inhibited as compared to the inflammatory lung injury in the absence of said prior administration of the anti-inflammatory agent, and wherein the anti-inflammatory agent consists of an A2A adenosine receptor agonist.

* * * * *